United States Patent
Bonnet et al.

(10) Patent No.: US 8,604,001 B2
(45) Date of Patent: *Dec. 10, 2013

(54) USE OF SULFATED OLIGOSACCHARIDES AS SLIMMING COSMETIC INGREDIENTS

(75) Inventors: Isabelle Bonnet, Lyons (FR); Nathalie Godard, Grezieu la Varenne (FR); Eric Perrier, Les Cotes d'Arey (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/429,478

(22) Filed: Mar. 26, 2012

(65) Prior Publication Data

US 2012/0184506 A1   Jul. 19, 2012

Related U.S. Application Data

(63) Continuation of application No. 12/164,268, filed on Jun. 30, 2008, now Pat. No. 8,153,611.

(60) Provisional application No. 61/010,332, filed on Jan. 8, 2008.

(30) Foreign Application Priority Data

Jun. 28, 2007 (FR) .................... 07 56112
Mar. 12, 2008 (FR) .................... 08 01348

(51) Int. Cl.
*A61Q 19/06* (2006.01)
*A61K 31/7016* (2006.01)
*A61K 31/702* (2006.01)
*A61K 31/7024* (2006.01)

(52) U.S. Cl.
USPC .................. 514/53; 514/61; 424/401

(58) Field of Classification Search
None
See application file for complete search history.

(56) References Cited

U.S. PATENT DOCUMENTS

| | | | |
|---|---|---|---|
| 4,525,359 A | 6/1985 | Greenway, III et al. | |
| 4,536,493 A | 8/1985 | Junge et al. | |
| 4,564,626 A | 1/1986 | Kreutner et al. | |
| 4,748,032 A | 5/1988 | Kono et al. | |
| 5,523,090 A | 6/1996 | Znaiden et al. | |
| 5,980,916 A | 11/1999 | Yvin et al. | |
| 6,025,360 A | 2/2000 | Miller et al. | |
| 6,143,730 A | 11/2000 | Parish et al. | |
| 2003/0045505 A1 | 3/2003 | Martinez et al. | |
| 2003/0143713 A1 | 7/2003 | Aghajari et al. | |
| 2003/0166609 A1 | 9/2003 | Yvin et al. | |
| 2004/0146539 A1 | 7/2004 | Gupta | |
| 2004/0224892 A1 | 11/2004 | Lubrano et al. | |
| 2006/0193814 A1 | 8/2006 | Ruvolo et al. | |
| 2007/0065386 A1 | 3/2007 | Lubrano et al. | |

FOREIGN PATENT DOCUMENTS

| | | |
|---|---|---|
| EP | 0 067 356 A1 | 12/1982 |
| FR | 2 719 846 A1 | 11/1995 |
| JP | 10-025234 A | 1/1998 |
| JP | 2000169325 A | 6/2000 |
| WO | WO-2006/048671 A1 | 5/2006 |

OTHER PUBLICATIONS

Guibet, M., et al., "Complete Assignment of $^1$H and $^{13}$C NMR Spectra of *Gigartina skottsbergii* λ-carrageenan Using Carrabiose Oligosaccharides Prepared by Enzymatic Hydrolysis", Carbohydrate Research, 2006, pp. 1859-1869.
Yuan, H., et al., "Preparation and invitro antioxidant activity . . . ", Carbohyd. Res., vol. 340, (2005), pp. 685-692.
Haumao, Y., et al., "Antioxidant Activity and Cytoprotective Effect of K-Carrageenan Oligosaccharides and Their Different Derivatives", Science Direct, www.sciencedirect.com and online source of Bioorganic & Medicinal Chemistry Letters, vol. 16, (2006), pp. 1329-1334.
PCT Search Report dated Sep. 17, 2008.
PCT Written Opinion dated Sep. 17, 2008.
Guibet, et al., "Complete Assignment of $^1$H and $^{13}$C NMR Spectra of *Gigartina skottsbergii* λ-Carrageenan Using Carragbiose Oligosaccharides Prepared by Enzymatic Hydrolysis", Carbohydrate Research, vol. 341, (2006), pp. 1859-1869.
French Search Report dated Feb. 28, 2008.

*Primary Examiner* — Leigh Maier
(74) *Attorney, Agent, or Firm* — Novak Druce Connolly Bove + Quigg LLP

(57) ABSTRACT

This invention relates to the use of a preparation comprising sulfated oligosaccharides which trap spermine or spermidine or both, as an active slimming ingredient in a cosmetic, pharmaceutical and/or nutraceutical composition. One of the objectives of the invention is to supply a cosmetic, pharmaceutical or nutraceutical composition with a slimming effect.

14 Claims, No Drawings

USE OF SULFATED OLIGOSACCHARIDES AS SLIMMING COSMETIC INGREDIENTS

CROSS-REFERENCE TO RELATED APPLICATIONS

This application is a continuation of U.S. patent application Ser. No. 12/164,268, filed Jun. 30, 2008, now U.S. Pat. No. 8,153,611, issued Apr. 10, 2012, which is incorporated by reference herein in its entirety, and which claims benefit of French Patent Application No. 0756112, filed Jun. 28, 2007, French Patent Application No. 0801348, filed Mar. 12, 2008, and U.S. Provisional Patent Application Ser. No. 61/010,332, filed Jan. 8, 2008.

BACKGROUND OF INVENTION

The invention relates to active slimming ingredients and an industrial process to prepare them.

An entire field of cosmetics and pharmacy is involved with active slimming ingredients. Various active ingredients in this field are intended to overcome problems like "orange peel skin" caused by adipocytes overloaded with fatty acids.

DESCRIPTION OF RELATED ART

Spermine and spermidine are polyamines which are present in adipose tissue and especially in adipocytes in average concentrations of 0.16 and 0.30 nmol/mg, respectively (Pedersen et al., 1989, Mol. Cell. Endocrinol, 62, 161-166).

In vitro, these polyamines have been demonstrated to stimulate three major enzymes of the lipogenesis process, a name given to the process of storing fatty acids in the form of triglycerides in the adipocytes. These enzymes are:
- sn-glycerol-3-phosphate acyltransferase or GPAT;
- 1.2-diacyl-sn-glycerol acyltransferase or DGAT;
- $Mg^{2+}$ phosphatidate phosphohydrolase or MGPPH.

In 1996, Jamdar et al. (1966, Enzyme Protein, 49, 222-230) discovered a correlation in obese rats between the concentrations of spermine and spermidine contained in adipose tissues and an increase in body fats. This increase correlates to a strong stimulation of the enzymes involved in the lipogenesis process, such as GPAT, DGAT or MGPPH, which demonstrates in vivo the significant involvement of polyamines in the fat storing process.

A fourth enzyme, lipoprotein lipase (or LPL) in charge of transporting fatty acids in the bloodstream to the adipocytes, also shows stimulation of its activity in the presence of spermine and spermidine (Giudicelli et al., 1976, FEBS Lett., 62, 1, 74-76).

Finally, spermine and spermidine have been identified as acting as "insulin-like" factors on the metabolism of adipocytes; meaning that these polyamines facilitate glucose transport, improve its conversion into triglycerides via stimulation of pyruvate dehydrogenase (Rutter et al., 1992, Biochem. J., 285, 435-439) and inhibit adipocytes lypolytic activities (Olefsky; et al. 1979, Horm. Metab. Res., 1.1, 209-213; Lockwood et al., J. Biol. Chem., 1974, 249, 24, 7717-7722; Richelsen et al., Biochem. J., 1989, 261, 2, 661-665).

Finally, Bethell et al., (1981, Biochim. Biophys. Res. Commun., 102, 1, 272-278) have shown that differentiation of fibroblasts in adipocytes is accompanied by a significant increase in the spermidine rate. This polyamine seems therefore to play an important role in the process of transforming fibroblasts into adipocytes.

Spermine and spermidine therefore foster the storage of fats in the adipocytes (via stimulation of the enzymes involved in the lipogenesis process) and inhibit the liberation of these fats (via inhibition of lipolysis). If these two polyamines are blocked, the expected effect would be an inhibition of the lipogenesis process and stimulation of lipolysis, resulting in an overall slimming effect.

To date, no active ingredient is known to act on spermine and/or spermidine.

BRIEF SUMMARY OF THE INVENTION

The main objective of the invention is to provide novel active slimming ingredients: which can be manufactured on an industrial scale.

This invention is especially intended to provide a mechanism for acting on spermine and/or spermidine, which are molecules involved in lipogenesis/lipolysis, especially at the adipocytes level. More particularly, it was desired to provide a slimming active ingredient having complementary structure to spermine and/or spermidine such that the slimming active ingredient was capable of forming a molecular trap for spermine and/or spermidine, thereby rendering at least some of these polyamines inactive.

This invention is intended to solve the above-described technical problems in an industrial, reproducible and reliable manner, at the lowest cost, especially in the cosmetic, nutriceutical and/or pharmaceutical fields.

DETAILED DESCRIPTION OF THE INVENTION

It was surprisingly discovered that compositions comprising one or several active ingredients capable of trapping spermine and/or spermidine can be prepared, and thus act on lipogenesis and/or lipolysis at the adipocytes level, especially in human beings.

Thus, this invention relates to substances which trap spermine and/or spermidine.

Trapping of spermine and/or spermidine enables not only reduction of lipogenesis and therefore a decrease in the storage of fats, but also an increase in lipolysis. This increase in lipolysis fosters the breakdown of fats. Thereby, the slimming active Ingredients of the present invention induce a twofold action towards a slimming effect.

When used herein "trapping of spermine and/or spermidine" means the association of spermine or spermidine, or both, with a compound capable of trapping spermine or spermidine, or both, by any sort of method, and preferably by complexation. In the description herein, such a compound may also be referred to as a "substance which traps spermine and/or spermidine".

Advantageously, a substance trapping spermine and/or spermidine in an efficient manner is a substance enabling inhibition of at least 50% of lipogenesis or stimulation of at least 50% of lipolysis, or both such inhibition and stimulation, a tested on normal human adipocytes in suspension.

Inhibition of lipogenesis is understood to be the decrease in storage of fats (e.g., lipids) in the adipocytes. Stimulation of lipolysis is understood to be an increase in the concentration of non-esterified fatty acids which have been freed from the adipocytes.

Among the screened potentially active substances, sulfated polysaccharides belonging to the family of sulfated galactans, as for example carrageenans or agars, have shown unexpected effectiveness.

Specifically, the sulfated polysaccharides having the best properties are the structures containing a maximum of 20 saccharidic units, and preferably a maximum of 10 saccharidic units.

These compounds can be advantageously prepared by hydrolysis of one or several sulfated polysaccharides.

Among these preferred polysaccharides or oligosaccharides, the kappa carrageenans are preferred for better results.

Two methods are advantageously utilized for hydrolysis of the carrageenans: Enzymatic hydrolysis done with carraghenases extracted from *Pseudomonas carrageenovora* (Knutsen et al., 2001, carbohydr. res., 331, 101-106)

Chemical hydrolysis: basic hydrolysis is generally slow and can result in ring openings. A hot reaction in the presence of hydrochloric acid (Ekstrom et al., 1983, carbohydr. Res. 116, 89-94) or sulfuric acid (Rochas et al., 1981, Polym. Bulletin. 5, 81-86) is preferred.

The oligosaccharides produced by the hydrolysis of the carrageenans are composed of chains of carrabiose units, neocarrabiose units and neocarratetraose units as shown in formula 1 below.

saccharide units. However, this invention is not limited to such a process. Thus another hydrolysis variation is used from iota and/or lambda carrageenan.

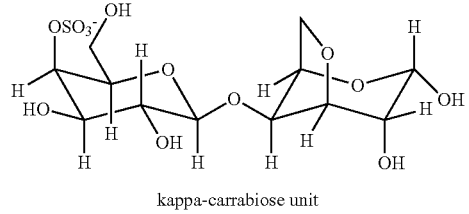

kappa-carrabiose unit

Formula 2

According to the nature and the concentration of the acid, the temperature and the reaction time, the oligosaccharide Formula 1 carrabiose, neocarrabiose and neocarratetraose

Generally, it is acknowledged that enzymatic hydrolysis of the carrageenans produce oligosaccharides comprising neocarrabiose units and that acid hydrolysis enable us to obtain oligosaccharides based on the carrabiose units (Kono et al., U.S. Pat. No. 4,748,032).

Advantageously, this invention relates to an improved hydrolysis process comprising introduction into a solution of at least one carrageenan, preferably for a sufficient duration and at a sufficient temperature to dissolve the carrageenans in the solvent medium, which is preferably water. The temperature is advantageously higher than 30° C.

The hydrolysis process advantageously comprises hydrolysis in an acid medium, by using, for example, a mineral acid such as hydrochloric acid. This hydrolysis is performed for a sufficient duration and at a sufficient temperature to hydrolyze the carrageenan into oligosaccharides. The pH of the reaction is advantageously less than 3, and preferably less than 2. It is generally preferable to perform hydrolysis of a carrageenan by an acid, such as a mineral acid like hydrochloric acid, for a duration of more than 5 hours, and preferably more than 10 hours, and even more preferably for a duration of more than 15 hours.

The reaction is advantageously stopped by the addition of a basic solution, by using for example a mineral base such as sodium hydroxide. The final pH of the preparation is generally from 3.5 to 5.

In one preferred embodiment, an acidic hydrolysis process from kappa-carrageenan is utilized. This process comprises an innovative variation prepared by the inventors in such a way as to obtain an optimal amount of kappa carrabiose units (cf. formula 2) comprising a beta-1.4 bond between the two solutions which are obtained present different concentrations of carrabioses and neocarratetraoses.

In the present invention, the oligosaccharide solutions which present a capability for trapping spermine and spermidine have a polymerization degree, or dp, between 2 (dp 1=one carrabiose unit) and 20, preferably between 2 and 10, and still even more preferably a maximum concentration of 2 dp units (or carrabioses).

Advantageously, following the hydrolysis process (chemical or enzymatic), all the insoluble parts are removed from the mixture, by centrifugation or by filtration.

If necessary, the oligosaccharide solutions can be purified for example by discoloration on active charcoal or ion exchange resins, or separated for example on membranes or gel chromatography.

The solutions can be transformed for example into powder especially by lyophilization, atomization, crystallization, etc.

The solution of sulfated oligosaccharides is composed advantageously of at least 0.1% carrabiose, advantageously at least 0.2% and preferably at least 0.5% (p/p), and generally does not comprise more than 10% (p/p) carrabiose, with respect to the weight of the total solution. The solution of sulfated oligosaccharides preferably comprises less than 1% of carrabioses. However, the solution of sulfated oligosaccharides can be lyophilized, thus enabling the production of a higher percentage of carrabiose as, for example, up to 30%, and even 40% (p/p) or more of the lyophilized composition.

This solution of sulfated oligosaccharides, which is considered in the present invention as being the active ingredient, can be diluted in the final composition. Typically, the solution of sulfated oligosaccharides is used at a concentration between about 0.01 and 10%, preferably between about 0.1 and 5% in weight of the final composition. Thus the final composition comprises a percentage of carrabiose generally between about $1.10^{-5}$ and 10%, preferably between about $2.10^{-5}$ and 0.1% by weight.

The solution of sulfated oligosaccharides advantageously presents a pH below 7, and preferably between 3.5 and 5.

The solution of oligosaccharides is usually a liquid composition, possibly in the form of a gel or hydrogel which is water based, but not exclusively. This solution can be an aqueous solution, possibly comprising different types of ions or solutions, and even insoluble or partially soluble compounds. This solution can also be a solution comprising solvents other than water, in which the sulfated oligosaccharides are soluble. The solvent is preferably acceptable on a dermatological basis.

The solutions of sulfated oligosaccharides (e.g., "slimming active ingredients") according to the present invention are used for the preparation of compositions, especially topical or orally administered compositions, and especially in the form of cosmetic, nutraceutical, dermo-pharmaceutical or pharmaceutical compositions. Thus, for these compositions, the excipient contains, for example, at least, one compound chosen from a group consisting of preservatives, emollients, emulsifiers, surfactants, moisturizers, thickeners, conditioners, matte finishing agents, stabilizers, antioxidants, texturizers, shining agents, film forming agents, solubilizing agents, pigments, dyes, perfumes and sunscreens. These excipients are preferably chosen from a group consisting of amino acids and their derivatives, polyglycerols, esters, polymers and cellulose derivatives, lanolin derivatives, phospholipids, lactoferrins, lactoperoxidases, sucrose based stabilizers, E vitamins and their derivatives, natural and synthetic waxes, vegetable oils, triglycerides, unsaponifiable matter, phytosterols, plant esters, silicones and their derivatives, protein hydrolysates, Jojoba oils and their derivatives, lipo/hydrosoluble esters, betains, aminoxides, plant extracts, esters of saccharose, titanium dioxide, glycines, parabens, and even preferably the group consisting of butylene glycol, steareth-2, stereath-21, glycol-15 stearyl ether, cetearyl alcohol, phenoxyethanol, methylparaben, ethylparaben, propylparaben, butylparaben, butylene glycol, natural tocopherols, glycerin, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, glycerol, bisabolol, a dimethicone, sodium hydroxide, PEG 30-dipolyhydroxysterate, capric/caprylic triglycerides, cetearyl octanoate, dibutyl adipate, grape seed oil, jojoba oil, magnesium sulphate, EDTA, a cyclomethicone, xanthan gum, citric acid, sodium lauryl sulphate, mineral waxes and mineral oils, isostearyl isostearate, dipelargonate of propylene glycol, isostearate of propylene glycol, PEG 8 beeswax, glycerides of hydrogenated palm oil, lanolin oil, sesame oil, cetyl lactate, lanolin alcohol, castor oil, titanium dioxide, lactose, saccharose, low density polyethylene, and isotonic saline solution.

Advantageously, the aforementioned compositions are formulated under a form chosen from the group consisting of a solution, aqueous or oil-based, a cream or an aqueous gel, or an oil-based gel, especially in a jar or tube, especially in a shower gel, a shampoo, a lotion, an emulsion, a micro-emulsion or a nano-emulsion, especially oil-in-water or water-in-oil or multiple or silicone; a lotion, especially in a glass bottle, in plastic or in a pump dispenser or in an aerosol; a vial; a liquid soap; a dermatological bar; an ointment; a foam; an anhydrous product, preferably liquid, paste or solid, for example in the form of a stick, notably a lipstick.

The terms "topical application", as used herein, mean applying or spraying the composition according to this invention on the skin surface or on the surface of mucous membranes.

The terms "dermatologically acceptable" as used herein, mean that the composition or the components of the composition are adapted to use in contact with human skin without unwarranted toxicity, incompatibility, instability, allergic response, or their equivalents.

Numerous cosmetically active ingredients are known by one skilled in the art to improve the health and/or the physical appearance of the skin and may be formulated by one skilled in the art into cosmetic or dermatological compositions to obtain the best effects. Furthermore, the slimming active ingredients described in the present invention can have a synergetic effect when combined one with other active ingredients. These combinations are also covered by this invention. The CFTA Cosmetic Ingredient Handbook Second Edition (1992) describes various classes of cosmetic and pharmaceutical ingredients that are frequently utilized in the cosmetic and pharmaceutical industry and which are particularly adapted to topical application. Some examples of these classes of ingredients include, but are not limited to, the following compounds: abrasive, absorbent, esthetic compounds such as perfumes, pigments, dyes, essential oils, astringents, etc. (for example, clove oil, menthol, camphor, eucalyptus oil, eugenol, menthyl lactate, hamelis distillate), anti-acne agents, anti-floculant agents, non foaming agents, anti-microbiotic agents (for example: Iodopropyl butylcarbamate), antioxidants, bonding agents, buffering agents, expanding agents, chelating, agents, additives, biocide agents, denaturing agents, external analgesics, film forming materials, polymers, opacifiers, pH adjusters, reducing agents, discoloring or clarifying agents (for example, hydroquinone, kojic acid, ascorbic acid, magnesium ascorbyl phosphate, ascorbyl glucosamine), conditioning agents (for example: hygroscopic agents), soothing agents for the skin and/or epulotics (for example: panthenol and its derivatives, for example: ethyl panthenol), Aloe vera, pantothenic acid and its derivatives, allantoine, bisabolol, and dipotassium of glycyrrhizinate), thickeners, vitamins and their derivatives or equivalents.

An advantageous embodiment of the present invention comprises the addition of at least one additional slimming active ingredient, notably chosen from a group consisting of inhibiting agent of phosphodiesterase enzyme, activating agent of adenylate cyclase, cyclic AMP or lipolytic derivatives and/or mixtures thereof.

Preferably, the present invention comprises the addition of at least caffeine or forskolin or theophyllin or theobromin or a combination thereof.

Different plant extracts generally used by formulating operators in slimming formulations such as for example root extract of *Coleus forskohlii*, bark extract of *Cecropia obtuse* or sea lettuce (*Uva lactuca*) can also be used as the additional slimming active ingredient.

It is particularly advantageous to combine the active ingredients of this invention with caffeine. It was discovered indeed, that these ingredients have complementary acting mechanisms. Preferably, caffeine, possibly in the form of derivatives and/or salts of caffeine acid, will be administered in combination with active ingredient according to the invention, at a dose between about 0.001% and 10% by weight of the total cosmetic, nutraceutical, or pharmaceutical composition, preferably between about 1 and 5%.

Combination of active ingredients according to the present invention with an activating agent of adenylate cyclase, in particular forskolin or a plant extract containing forskolin is particularly advantageous.

In one preferred embodiment, forskolin, for example as Coleus forskohlii extract or Plectanthus barbatus extract, will be administrated in combination with active ingredients according to the present invention at dosages between about 0.001% and 1%, preferably between about 0.05% to 0.25% by weight: of the total composition.

This invention thus relates to a method of slimming cosmetic care comprising the use of at least one active ingredient according to the present invention, alone or in combination with an additional slimming active ingredient as discussed above, or of a cosmetic composition comprising such slimming active ingredient of the present invention, as referenced above or hereafter. This cosmetic care includes the topical application of the active ingredient on the cutaneous areas to be treated. In one embodiment, this cosmetic care can be formulated in the form of a nutraceutical composition (oral administration).

This invention also relates to a method of therapeutic treatment to reduce the amount of lipids stored by the adipocytes, including especially the administration or the topical application of at least one active ingredient, or of one cosmetic composition comprising such an active ingredient, as referenced above or hereafter. The treatment advantageously combines both a decrease in lipogenesis and an increase in lipolysis.

This invention further relates to a method of producing a slimmer appearance to a part of a human body comprising the oral or topical application of at least one slimming active ingredient of the present invention, or a cosmetic, nutraceutical, or pharmaceutical composition comprising such slimming active ingredient to a human body in need thereof.

Other objectives, characteristics and advantages of the invention will be clearly apparent for one skilled in the art when reading the explanatory description which refers to examples which are given only for the purposes of illustration and which in no way are intended to limit the scope of the invention.

The examples are an integral part of this invention and any characteristic which seems new with respect to any previous state of the art taken from the description in its entirety, including the examples, is an integral part of the invention in its function and in its generality.

Thus, each example is general in scope.

Furthermore, in the examples, all percentages are given in weight, unless otherwise indicated, and the temperature is expressed in Celsius degree unless otherwise indicated, and pressure is atmospheric pressure, unless otherwise indicated.

EXAMPLES

Example 1

Preparation of the Oligosaccharides 38.5 mL of pure laboratory water was heated to 60° C. 0.49 g of sodium chloride was added, as well as 1.67 g of kappa-carrageenans. The solution was left under agitation, at 60° C. for 25 minutes. The hydrolysis reaction was initialized by the addition of 8.33 g of a solution of a 1 N of hydrochloric acid and the mixture was maintained at a temperature of 60° C. during the entire process. At the time of desired hydrolysis, the reaction was then stopped by the addition of 9 mL of a solution of 1 N sodium hydroxide. The pH of the preparation was therefore between 4 and 4.5. The solution was then filtered through a 500 nm filter and then preservatives, as well as a gelling agent, can be added to the preparation.

In most of the following examples, the experiments were performed on the filtrate (without a preservative and without gelling agent).

Example 2

Evolution of the Composition of the Oligosaccharides Preparations with Regard to Hydrolysis Time Sulfated oligosaccharide solutions were prepared according to example 1, with hydrolysis times of 2.4 and 16 hours.

These solutions were then analyzed by HPLC (Waters Alliance 2685, column TSK gel 2000 PWXL) equipped with a refractometer detector. A standard range of glucose was analyzed in parallel, which thus enables to know the composition of our mixture in terms of carrabiose and neocarratetraose.

The results, presented in table 1, show that the longer is the hydrolysis time, the more significant the concentration of carrabiose will be.

TABLE 1

| Hydrolysis time (hours) | % carrabiose | % neocarratetraose |
|---|---|---|
| 2 | 0.106 | 0.228 |
| 5 | 0.365 | 0.180 |
| 16 | 0.890 | 0.043 |

% of carrabiose or neocarratetraose indicated in % by weight, based on the total filtrate weight, said filtrate being adjusted at a pH between 4 and 4, 5.

Example 3

In Vitro Demonstration of the Effectiveness of Oligosaccharides on the Trapping of Spermine, and Spermidine Principle: If spermine and spermidine are put in the presence of deoxyribonucleic acid (DNA), precipitation of DNA is then observed and the optic density of the mixture, read at 600 nm, increases very significantly.

If a compound which "traps" spermine or spermidine is added beforehand to the solution of said polyamine, no precipitation appears when the DNA solution is added.

We can then calculate a percentage of protection provided by the tested active ingredient in terms of the DNA precipitation induced by the polyamines.

Protocol:

0.4 g of fish DNA (Sigma) is added to 160 g of a pH6 phosphate buffer (0.06 M potassium phosphate and 0.001 M sodium phosphate).

10 µL of an aqueous solution of 50 mM of spermine (Sigma) is distributed into each well of a 96-well plate:

Then the following is distributed:
  90 µL of a solution of sulfated oligosaccharides (active ingredient) or of an aqueous solution of 150 mM of adenosine triphosphate (or ATP, Sigma)
  or 90 µL of pure laboratory water (in the "control" wells or "100%" wells)

The plate is left under agitation for 5 minutes at room temperature, then 100 µL of the DNA solution is added to all of the wells.

After 5 seconds of manual agitation, the optic density of the well is read at 600 nm.

The percentage of protection provided by the active ingredient in terms of the precipitation of the DNA in the presence of spermine is calculated as follows:

% protection=100−[($OD_{Active\ or\ ATP}/OD_{100\%}$)×100]

By "$OD_{Active\ or\ ATP}$" we mean the optic density of the well containing DNA, spermine or spermidine, and the Active Ingredient or the ATP after reaction. "OD 100%" means the optic density of the well containing DNA and spermine or spermidine, after precipitation.

The more significant the protection percentage is, the greater is the "trapping" of spermine by the active ingredient and the lesser is the DNA precipitation.

The same experiment can be: performed by replacing the solution of 50 mM spermine with an aqueous solution of 300 mM spermidine (Sigma).

Oligosaccharides solutions were produced according to example 1, with 2, 5 and 16 hours of hydrolysis time. After dilution at 10% in pure laboratory water, the different solutions were tested. The results are given in table 2 below:

TABLE 2

| Hydrolysis time | % spermine protection | % spermidine protection |
|---|---|---|
| 2 | 3.9 | 29.9 |
| 5 | 4.5 | 28.2 |
| 16 | 10.3 | 34.3 |

The longer the hydrolysis time is, the richer the oligosaccharides solution is in carrabiose and the bigger is the trapping action of the spermine and spermidine.

Thus active ingredients containing at least 0.2% of carrabiose are preferred, and even more preferred, at least 0.5% by weight of the solution of sulfated oligosaccharides.

Example 4

Comparison of the Carrabiose Rate after Hydrolysis of Various Sulfated Galactans Solutions of sulfated oligosaccharides were prepared using kappa, iota and lambda carrageenans and agar according to example 1, with a hydrolysis time of 16 hours.

The extracts were then analyzed by HPLC according to the technique described in example 2, with the exception of agar hydrolysates which couldn't be analyzed under the same conditions (agarobiose units). After dilution at 3% in pure laboratory water, a trapping test of the spermidine was performed, according to the protocol described in Example 3.

TABLE 3

| Hydrolyzed galactans | % Trapping | % Carrabiose | % Neocarratetraose |
|---|---|---|---|
| Kappa-carrageenans | 16.1% | 0.878 | 0.155 |
| Iota-carrageenans | 13.1% | 0.292 | 0.344 |
| Lamda-carrageenans | 13.5% | 0.179 | 0.197 |
| Agar | 8.9% | Not applicable | Not applicable |

The carrageenan hydrolysates (kappa, iota and lambda) show the best effectiveness in terms of trapping spermidine. This trapping is correlated at a percentage of carrabioses in the product.

Example 5

Demonstration of the Effectiveness of Oligosaccharides on the Inhibition of Lipogenesis in Normal Human Adipocytes The ex vivo inhibition of lipogenesis was evaluated in suspensions of human adipocytes which were isolated from a sampling taken during an abdominal plasty performed on a 42 year old woman.

The adipocytes suspension was incubated for one hour at 37° C. with 3 or 5% of a solution of sulfated oligosaccharides prepared according to example 1 (hydrolysis time: 16 hours), or with a standard study solution (1 mM theophylline or caffeine), on in the absence of these solutions (control).

Each assay was done in triplicate.

A radioactive marker [2-$^{14}$C] acetate was then added to the various assays at a concentration of 2.5 µCi/mL.

After 4 hours of incubation at 37.degree. C., the lipids were extracted by a methanol/chloroform/water mixture and then dehydrated. The radioactivity, expressed in counts per minute (cpm), is then quantified through liquid scintigraphy (LKB 1210 Rackbeta).

The results: are given in table 4 below. The statistical analysis was performed according to the Dunnett's multiple comparison test.

TABLE 4

| Treatment | Concentration in water | cpm | Standard deviation | % Control | p |
|---|---|---|---|---|---|
| Control | — | 472253 | 4474 | 100 | — |
| Theophylline | 1 mM | 27225 | 6195 | 6 | P < 0.01 |
| Caffeine | 1 mM | 20741 | 2932 | 4 | P < 0.01 |
| Sulfated | 5% | 109647 | 7064 | 23 | P < 0.01 |
| Oligosaccharides | 3% | 97139 | 9691 | 21 | P < 0.01 |

According to the experimental conditions, the solution of sulfated oligosaccharides tested at 3% to 5% significantly inhibits lipogenesis and in a dose-dependent manner.

Example 6

Demonstration of the Effectiveness of the Preparation on the Stimulation of Lipolysis, in Normal Human Adipocytes The lipolysis stimulation activity was evaluated in suspensions of human adipocytes isolated from a sample taken during an abdominal plasty performed on a 34 year old woman.

The adipocytes suspension was incubated, for 2 hours at 37° C. with 3 or 5% of a solution of sulfated oligosaccharides prepared according to example 1 (16 hours of, hydrolysis time) in percentage of total weight of the culture, or with standard study solutions (1 mM theophylline or caffeine) or in the absence of solutions (control). Each assay was performed 6 times.

At the end of the incubation period, the Non-Esterified Fatty Acids (NEFA) which were; present in the incubation mediums were measured with commercially available dosage kits (OXOID 46 551). The results are given in Table 5 below.

TABLE 5

| Treatment | Conc. | NEFA in μM | Standard deviation | % Control | p |
|---|---|---|---|---|---|
| Control | — | 96 | 6 | 100 | |
| Theophylline | 1 mM | 537 | 45 | 560 | P < 0.01 |
| Caffeine | 1 mM | 525 | 40 | 547 | P < 0.01 |
| Sulfated | 5% | 200 | 10 | 209 | P < 0.01 |
| Oligosaccharides | 3% | 180 | 12 | 187 | P < 0.01 |

According to the experimental conditions, the solution of sulfated oligosaccharides tested at 3% and 5% significantly stimulates lipolysis and in a dose-dependent manner.

Example 7

Demonstration of a Slimming Effect of the Oligosaccharides According to the Invention in Combination with Caffeine The slimming effectiveness of a hydro-alcohol gel containing a mixture of "3% caffeine+3% of a solution of sulfated oligosaccharides prepared according to example 1 (16 hours of hydrolysis time)" was compared to a hydro-alcohol gel containing 3% caffeine.

The products were applied to the thighs of healthy volunteers and the slimming effect was evaluated over an 8 weeks period by measuring in centimeters.

In practice, 25 volunteers aged 21 to 49 were selected and tested according to specific criteria (Body Mass Index, presence of cellulite). The weight of each volunteer was monitored during the entire study and couldn't vary from ±2 kg. The products were applied according to a randomization of right thigh/left thigh: one thigh treated by the association (caffeine+oligosaccharides solution) and one thigh treated by caffeine. The gels were applied twice a day for 8 consecutive weeks, using small circular movements until the entire product was absorbed.

The chosen formulation for this study was a hydro-alcohol gel on the basis of a ratio of 750/water to 25% denatured alcohol.

Measurement in centimeters of the thighs circumference was done at the middle of the volunteers' thighs using a tape measure applied without compression by the same technician for the entire study.

A laser range-finding system for the measurement zones was used to ensure that same positioning for each thigh evaluated was reproduced and precise.

The measurements were performed before application of the products (T0) and then after 14 days, 1 month and 2 months. The results of this study are in Table 6 below.

TABLE 6

| Time | Caffeine | Caffeine + sulfated oligosaccharides | Significance of results ("Caffeine + sulfated oligosaccharides" versus "caffeine") |
|---|---|---|---|
| 14 days | 0 cm | −0.1 cm | Not significant |
| 28 days | −0.1 cm | −0.4 cm | p < 0.001 |
| 56 days | −0.3 cm | −0.6 cm | p < 0.01 |

After only 14 treatment days, a decrease in the circumference of the volunteers' thighs having received applications of the gel containing the caffeine and the sulfated oligosaccharides was observed. It should be noted that the gel containing caffeine alone had no slimming effect.

This excellent effectiveness due to the combination of caffeine and sulfated oligosaccharides is even more evident after 28 and 56 days of treatment.

Indeed, at 56 days, the average decrease of the circumference of the thigh is 0.6 cm for the volunteers using the caffeine+oligosaccharide gel, while the decrease is only 0.3 cm for the volunteers who applied the caffeine gel (significant difference, p<0.01).

Example 8

Utilization of the Products of the Invention in Cosmetic or Pharmaceutical Formulations of the Type "Oil Emulsion in Water"

Formulation 8a:

| | | |
|---|---|---|
| A | Water | qsp 100 |
| | Butylene Glycol | 2 |
| | Glycerin | 3 |
| | Sodium Dihydroxycetyl Phosphate, Isopropyl Hydroxycetyl Ether | 2 |
| B | Glycol Stearate SE | 14 |
| | Triisononaoin | 5 |
| | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 8b:

| | | |
|---|---|---|
| A | Water | qsp 100 |
| | Butylene Glycol | 2 |
| | Glycerin | 3 |
| | Polyacrylamide, Isoparaffin, Laureth-7 | 2.8 |
| B | Butylene Glycol, Methylparaben, Ethylparaben, Propylparaben; | 2 |
| | Phenoxyethanol, Methylparaben, Propylparaben, Butylparaben, Ethylparaben | 2 |
| | Butylene Glycol | 0.5 |
| D | Products of the invention | 0.01-10% |

Formulation 8c:

| | | |
|---|---|---|
| A | Carbomer | 0.50 |
| | Propylene Glycol | 3 |
| | Glycerol | 5 |
| | Eau | qsp 100 |
| B | Octyl Cocoate | 5 |
| | Bisabolol | 0.30 |
| | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-10% |

Example 9

Utilization of the Products of the Invention in a Formulation of Type "Water in Oil"

| | | |
|---|---|---|
| A | PEG 30-dipolyhydroxystearate | 3 |
| | Capric Triglycerides | 3 |
| | Cetearyl Octanoate | 4 |
| | Dibutyl Adipate | 3 |
| | Grape Seed Oil | 1.5 |
| | Jojoba Oil | 1.5 |
| | Phenoxyethanol, Methylparaben, Propylparaben, Butylparaben, Ethylparaben | 0.5 |
| B | Glycerin | 3 |
| | Butylene Glycol | 3 |
| | Magnesium Sulfate | 0.5 |
| | EDTA | 0.05 |
| | Water | qsp 100 |
| C | Cyclomethicone | 1 |
| | Dimethicone | 1 |
| D | Perfume | 0.3 |
| E | Products of the invention | 0.01-10% |

Example 10

Utilization of Products of the Invention in a Formulation of Type "Shampoo or Shower Gel"

| | | |
|---|---|---|
| A | Xantham Gum | 0.8 |
| | Water | qsp 100 |
| B | Butylene Glycol, Methylparaben, Ethylparaben, Propylparaben | 0.5 |
| | Phenoxyethanol, Methylparaben, Propylparaben, Butylparaben, Ethylparaben | 0.5 |
| C | Citric acid | 0.8 |
| D | Sodium Laureth Sulfate | 40.0 |
| E | Product of the invention | 0.01-10% |

Example 11

Utilization of Products of the Invention in a Formulation of Aqueous Gels

| | | |
|---|---|---|
| A | Water | qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01-10% |

Example 12

Utilization of Products of the Invention in a Formulation Type "Triple Emulsion"

| | Primary emulsion W1/O | |
|---|---|---|
| A | PEG 30-dipolyhydroxystearate | 4 |
| | Capric Triglycerides | 7.5 |
| | Isohexadecane | 15 |
| | PPG-15 Stearyl ether | 7.5 |
| B | Product of the invention | 0.01-10% |
| | Water | Qsp 65.3 |
| C | Phenoxyethanol, Methylparaben, Propylparaben, Butylparaben, Ethylparaben | 0.7 |
| | Secondary emulsion W1/O/W2 | |
| A | Primary emulsion | 60 |
| B | Poloxamer 407 | 2 |
| | Phenoxyethanol, Methylparaben, Propylparaben,2-bromo-2nitropropane-1,3 diol | 0.3 |
| | water | qsp 100 |
| C | Carbomer | 15 |
| D | Triethanolamine | PH 6.0-6.5 |

Example 13

Preparation of Pharmaceutical Formulations Containing the Product of the Invention Formulation 13a: Preparation in Tablet Form

| | | |
|---|---|---|
| A | Excipients | In g per tablet |
| | Lactose | 0.359 |
| | Saccharose | 0.240 |
| B | Products of the invention* | 0.001-0.1 |

*The product of the invention is obtained, for example, according to the extraction process described in Example 1 (16 hours of hydrolysis time) followed by a drying stage.

Formulation 13b: Preparation of an Ointment

| | | |
|---|---|---|
| A | Excipients | |
| | Low density polyethylene | 5.5 |
| | Liquid paraffin | qsp 100 |
| B | Products of the invention* | 0.001-0.1 |

*The product of the invention is obtained, for example, according to the extraction process described in example 1 (16 hours of hydrolysis time) followed by a drying stage.

Formulation 13c: Preparation of an Injectable Formula

| | | |
|---|---|---|
| A | Excipient | |
| | Isotonic salt solution | 5 mL |
| | Products of the invention* | 0.001-0.1 g |

*The product of the invention is obtained, for example, according to the extraction process described in example I (16 hours of hydrolysis time) 'followed by a drying stage.

Example 14

Use of One Embodiment of the Invention in a Hydroalcoholic Gel

In a main vessel, water, SDA alcohol 40B, xanthan gum, carbomer, and hydroethylcellulose were premixed until fully hydrated. Pentylene glycol, butylene glycol, and AMS LEUCIDAL® Liquid (available from Active Concepts, LLC) were added, in order, and the composition was mixed in a homomixer until uniform. VELVESIL® 125-01P (available from GE Silicones), dimethicone, DC 5225C Formulation Aid (available from Dow Corning) were added, in order, and the resulting composition was mixed until uniform.

SEPIGEL 305® (available from Seppic) and PHENOXETOL® were added, in order, to the homomixer. 3%, by weight (based on the final composition), of a hydroglycolic solution of hydrolyzed carrageenan according to the present invention was dispersed in water, then added to the homomixer.

Water and a 30% sodium hydroxide solution were premixed and added to the homomixer to produce the final composition.

The invention claimed is:

1. A method of trapping spermine or spermidine or both, comprising topically applying or orally administering a composition comprising a solution of sulfated oligosaccharides having a polymerization degree of between 2 and 20 at a concentration of about 0.01% to 10% by weight of the composition, wherein the solution of sulfated oligosaccharides is capable of trapping spermine or spermidine or both, and comprises at least 0.1% of carrabiose with respect to the total weight of the solution.

2. The method of claim 1, wherein the sulfated oligosaccharides are composed of a maximum of 20 galactose units.

3. The method of claim 1, wherein the solution of sulfated oligosaccharides is obtained by hydrolysis of a polysaccharide comprising a sulfated galactan.

4. The method of claim 1, wherein the solution of sulfated oligosaccharides comprises an oligosaccharide based on neo-carratetraose.

5. The method of claim 1, wherein the solution of sulfated oligosaccharides has a polymerization degree (dp) of 2 to 10 dp units.

6. The method of claim 1, wherein the sulfated oligosaccharides comprise a kappa carrageenan.

7. The method of claim 1, wherein the solution of sulfated oligosaccharides is obtained from a kappa carrageenan by an acidic hydrolysis process.

8. The method of claim 1, wherein the solution of sulfated oligosaccharides comprises 0.5% to 1% carrabiose with respect to the total weight of the solution.

9. The method of claim 1, wherein the solution of sulfated oligosaccharides comprises 0.1% to 10% carrabiose with respect to the total weight of the solution.

10. The method of claim 1, wherein the topical application or oral administration of the composition results in a slimming effect.

11. The method of claim 1, wherein the composition is a cosmetic, nutraceutical, or pharmaceutical composition.

12. The method of claim 1, wherein the topical application or oral administration of the composition results in decreased lipogenesis or increased lipolysis in adipocytes.

13. The method of claim 1, wherein the topical application or oral administration of the composition produces a slimmer appearance to a part of a human body, wherein the solution of sulfated oligosaccharides inhibits at least 50% of lipogenesis or stimulates at least 50% of lipolysis or both, when tested on normal human adipocytes in suspension.

14. The method of claim 1, wherein the solution of sulfated oligosaccharides is an active slimming ingredient.

* * * * *